United States Patent
Ota et al.

(10) Patent No.: US 9,834,502 B2
(45) Date of Patent: Dec. 5, 2017

(54) METHOD FOR PRODUCING CATIONIC LIPID

(71) Applicant: NOF CORPORATION, Tokyo (JP)

(72) Inventors: Masaki Ota, Kawasaki (JP); Ken Hamura, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/529,324

(22) PCT Filed: Dec. 8, 2015

(86) PCT No.: PCT/JP2015/084345
§ 371 (c)(1),
(2) Date: May 24, 2017

(87) PCT Pub. No.: WO2016/093205
PCT Pub. Date: Jun. 16, 2016

(65) Prior Publication Data
US 2017/0275242 A1 Sep. 28, 2017

(30) Foreign Application Priority Data
Dec. 8, 2014 (JP) .................................. 2014-247723

(51) Int. Cl.
C07C 227/00 (2006.01)
C07C 213/08 (2006.01)

(52) U.S. Cl.
CPC .................. C07C 213/08 (2013.01)

(58) Field of Classification Search
CPC .................................................. C07C 213/08
(Continued)

(56) References Cited

U.S. PATENT DOCUMENTS 5,264,618 A 11/1993 Felgner et al.
5,459,127 A 10/1995 Felgner et al.
(Continued)

FOREIGN PATENT DOCUMENTS

JP 5-508626 A 12/1993
JP 2002-515024 A 5/2002
(Continued)

OTHER PUBLICATIONS

International Search Report, issued by International Searching Authority in corresponding International Application No. PCT/JP2015/084345, mailed on Feb. 23, 2016, (PCT/ISA/210).
(Continued)

*Primary Examiner* — Deborah D Carr
(74) *Attorney, Agent, or Firm* — Sughrue Mion, PLLC

(57) ABSTRACT

A method for producing a cationic lipid, wherein a cationic lipid represented by formula (1) is mixed with a tetraalkylammonium salt having $X^-$ in an organic solvent, and a filtrate obtained by separating a tetraalkylammonium iodide deposited by filtration is concentrated to deposit a tetraalkylammonium iodide, thereby obtaining a cationic lipid represented by formula (2):

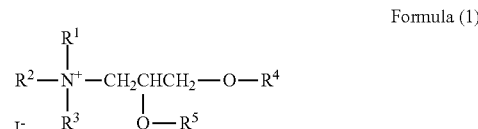

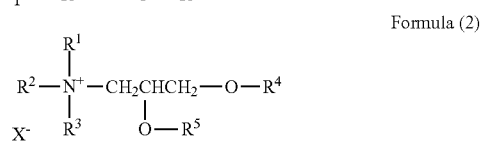

wherein $R^1$ to $R^5$ and $X^-$ are as defined herein.

4 Claims, 3 Drawing Sheets

(58) Field of Classification Search
USPC .......................................................... 554/114
See application file for complete search history.

(56) References Cited

U.S. PATENT DOCUMENTS

| | | | |
|---|---|---|---|
| 5,824,812 | A | 10/1998 | Nantz et al. |
| 5,869,715 | A | 2/1999 | Nantz et al. |
| 5,925,623 | A | 7/1999 | Nantz et al. |
| 2011/0045473 | A1 | 2/2011 | De Fougerolles et al. |
| 2011/0097720 | A1 | 4/2011 | Ciufolini et al. |
| 2011/0117125 | A1 | 5/2011 | Hope et al. |
| 2012/0225434 | A1 | 9/2012 | Ciufolini et al. |
| 2014/0295449 | A1 | 10/2014 | Ciufolini et al. |
| 2016/0274089 | A1 | 9/2016 | Ciufolini et al. |

FOREIGN PATENT DOCUMENTS

| | | |
|---|---|---|
| JP | 2011-509258 A | 3/2011 |
| JP | 2014-132014 A | 7/2014 |
| WO | 2007/022030 A2 | 2/2007 |
| WO | 2008/148057 A2 | 12/2008 |

OTHER PUBLICATIONS

Alfred M. Aberle et al., "The counterion influence on cationic lipid-mediated transfection of plasmid DNA", Rapid report, Elsevier, Biochimica et Biophysica Acta 1299 (1996) (pp. 281-283, 3 Pages Total).

Philip L. Felgner et al., "Lipofection: A highly efficient, lipid-mediated DNA-transfection procedure", Proc. Natl. Acad. Sci., USA, vol. 84, Biochemistry, Nov. 1987 (pp. 7413-7417, 5 Pages Total).

ETHOD FOR PRODUCING CATIONIC
LIPID

TECHNICAL FIELD

The present invention relates to a method for producing a cationic lipid.

BACKGROUND ART

Nucleic acid drugs have been attracting attention as drugs of next generation, but in order to efficiently introduce nucleic acids into cells, a carrier is required. The carrier is roughly divided into a virus carrier and a non-virus carrier. The virus carrier has a high introduction efficiency of nucleic acid in comparison with the non-virus carrier, but cannot solve the problem of toxicity. Therefore, the non-virus carrier has been attracting attention because it has high safety although the introduction efficiency is inferior to the virus carrier.

As the non-virus carrier, a carrier using a lipid membrane composed of a cationic lipid, a PEG lipid or the like and a carrier using a micelle composed of a cationic polymer have been reported, and investigations on the carrier using a lipid membrane which can control the function by the composition of the lipid have been actively made. Of the lipids for use in the lipid membrane, the lipid which most affects the introduction efficiency of nucleic acid is a cationic lipid.

The cationic lipid ordinarily has one quaternary ammonium group and two hydrophobic groups. Typical cationic lipid includes N-[1-(2,3-dioleoyloxy)propyl]-N,N,N-trimethylammonium chloride (hereinafter DOTAP-Cl) and N-[1-(2,3-dioleyloxy)propyl]-N,N,N-trimethylammonium chloride (hereinafter DOTMA-Cl). These lipids are the cationic lipids most widely used because of the high introduction efficiency of nucleic acid in comparison with other known cationic lipids.

DOTAP-Cl and DOTMA-Cl are obtained by introducing an oleoyl group or an oleyl group into dimethylaminopropanediol and then subjecting to quaternization with methyl chloride (Non-Patent Document 1). However, since methyl chloride is gas under normal temperature and atmospheric pressure, it must be used in a high-pressure reaction vessel, for example, an autoclave. In addition, since methyl chloride is highly virulent, there is a drawback in that particular attention to safety must be paid to its handling and a device for use.

For the reason described above, a method for producing DOTAP-Cl or DOTMA-Cl without using methyl chloride has been developed and reported. In Non-Patent Document 2, an oleoyl group is introduced into dimethylaminopropanediol, N-[1-(2,3-dioleyloxy)propyl]-N,N,N-trimethylammonium iodide (hereinafter DOTAP-I) is synthesized by using methyl iodide, and then the iodide ion of DOTAP-I is exchanged with a chloride ion by a column packed with an ion exchange resin.

However, the method described in Non-Patent Document 2 requires a large amount of ion exchange resin to the lipid obtained. Moreover, in order to perform efficient anion exchange, since the concentration of DOTAP-I in the solution must be diluted, it is necessary to dissolve DOTAP-I in a large amount of the solvent so that the production scale becomes very large. In addition, since a large amount of the solvent must be removed after the anion exchange in the ion exchange column, the method is inefficient and not preferred industrially.

Therefore, in Patent Document 1, anion exchange is carried out by repeating four times the operation of adding a methanol solution of 1 N hydrochloric acid to a dichloromethane solution of N-[1-(2,3-dilinoleoyloxy)propyl]-N,N,N-trimethylammonium iodide or N-[1-(2,3-dilinoleyloxy)propyl]-N,N,N-trimethylammonium iodide, stirring and washing with a sodium chloride solution. However, this method not only has a low anion exchange ratio but also requires an inefficient purification step, for example, column purification, in order to obtain a product having the purity required for pharmaceutical, because in the case of having an ester bond in the molecule as in DOTAP-Cl, an impurity, for example, a fatty acid is generated by hydrolysis with an acid.

PRIOR ART DOCUMENT

Non-patent Document

Non-Patent Document 1: Biochem., 84, 7413 (1987)
Non-Patent Document 2: Biochim. Biophys. Acta, 1299, 281 (1996)

Patent Document

Patent Document 1: JP-A-2014-132014

SUMMARY OF THE INVENTION

Problems that the Invention is to Solve

As described above, the method for producing a cationic lipid which has been reported to date is a production method requiring a special production equipment or an extremely inefficient production method including an ion exchange column, and an efficient industrial production method of a cationic lipid of high purity has not been established.

An object of the present invention is to provide an industrial method for producing a cationic lipid, which does not require a special equipment and by which a cationic lipid of high purity can be efficiently obtained.

Means for Solving the Problems

In a common equilibrium reaction, the equilibrium can be inclined to one direction by discharging the product out of the reaction system. For example, in the Finkelstein reaction for obtaining an alkyl iodide from various alkyl halides, the reaction proceeds due to deposition of sodium salt by-produced.

Therefore, as a result of the intensive investigations forcing on the fact that the anion exchange is an equilibrium reaction, the inventors have found that when a cationic lipid represented by formula (1) is reacted with a tetraalkylammonium salt having an arbitrary anion in an organic solvent, tetraalkylammonium iodide formed by anion exchange is deposited so that the reaction proceeds efficiently, and thereafter the tetraalkylammonium iodide is removed by filtration and the filtrate is concentrated to increase the anion exchange ratio, thereby completing the invention.

A method for producing a cationic lipid according to the invention is characterized by that a cationic lipid represented by formula (1) is mixed with a tetraalkylammonium salt having $X^-$ in an organic solvent, and after separating a tetraalkylammonium iodide deposited by filtration to obtain a filtrate, the filtrate is concentrated to deposit at least a tetraalkylammonium iodide, thereby obtaining a cationic lipid represented by formula (2):

$$\begin{array}{c} R^1 \\ | \\ R^2—N^+—CH_2CHCH_2—O—R^4 \\ | \quad | \\ I^- \quad R^3 \quad O—R^5 \end{array}$$

Formula (1)

wherein, in the formula (1), $R^2$ and $R^3$ each represents a hydrocarbon group having from 1 to 6 carbon atoms, and $R^4$ and $R^5$ each represents an acyl having from 10 to 22 carbon atoms or a hydrocarbon group having from 10 to 22 carbon atoms;

$$\begin{array}{c} R^1 \\ | \\ R^2—N^+—CH_2CHCH_2—O—R^4 \\ | \quad | \\ X^- \quad R^3 \quad O—R^5 \end{array}$$

Formula (2)

wherein, in the formula (2), $R^1$, $R^2$ and $R^3$ each represents a hydrocarbon group having from 1 to 6 carbon atoms, $R^4$ and $R^5$ each represents an acyl having from 10 to 22 carbon atoms or a hydrocarbon group having from 10 to 22 carbon atoms, and $X^-$ represents a chloride ion, a bromide ion, a fluoride ion, an acetate ion, a methanesulfonate ion or a p-toluenesulfonate ion.

Advantage of the Invention

The invention is extremely useful as an industrial method for producing a cationic lipid because a cationic lipid of high purity can be efficiently obtained without requiring a special equipment.

Figure 1:
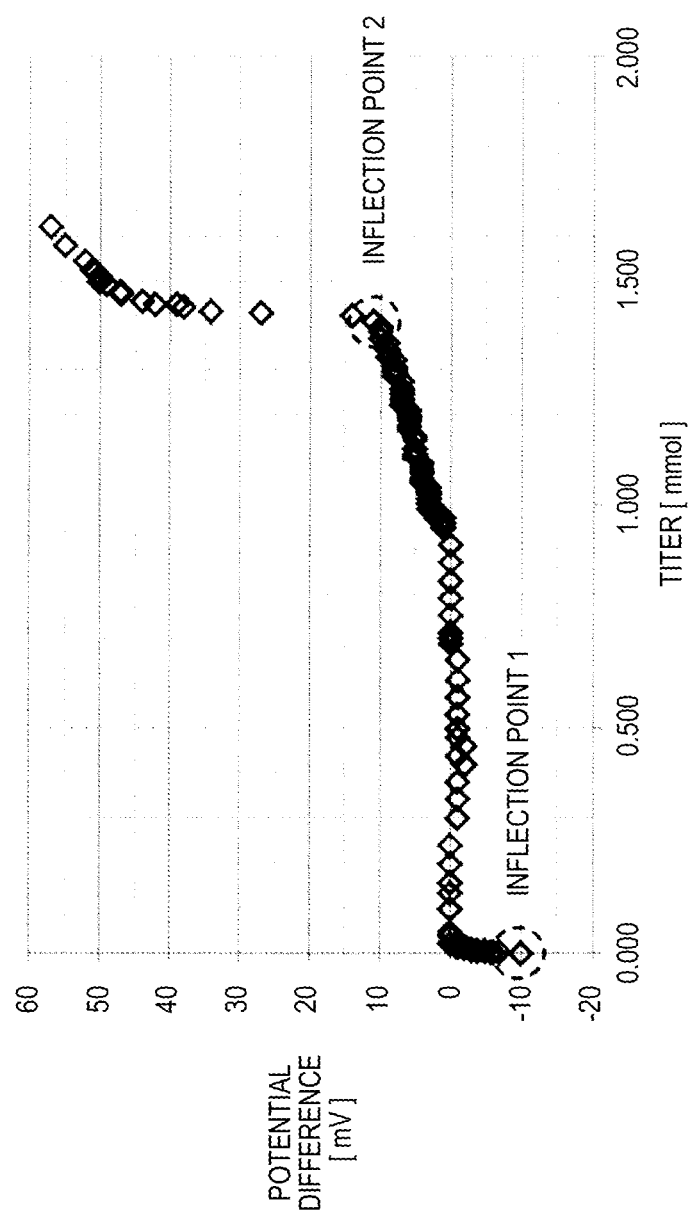
FIG. 1 shows the titration result of DOTAP-Cl obtained in Example 1.

MODE FOR CARRYING OUT THE INVENTION $R^1$ to $R^3$ in formula (1) or formula (2) each represents a hydrocarbon group having from 1 to 6 carbon atoms. Each of $R^1$ to $R^3$ may be straight-chain, branched or cyclic, or $R^1$ and $R^2$ may be bonded to each other to form a ring. $R^1$ to $R^3$ may be the same or different from each other. The number of carbon atoms in the hydrocarbon group is preferably from 1 to 3, and more preferably 1.

The hydrocarbon group having from 1 to 6 carbon atoms constituting each of $R^1$ to $R^3$ specifically includes, for example, a methyl group, an ethyl group, a propyl group, an isopropyl group, a n-butyl group, a sec-butyl group, an isobutyl group, a tert-butyl group, a pentyl group, an isopentyl group, a neopentyl group, a tert-pentyl group, a 1,2-dimethylpropyl group, a 2-methylbutyl group, a 2-methylpentyl group, a 3-methylpentyl group, a 2,2-dimethylbutyl group, a 2,3-dimethylbutyl group, a cyclopentyl group, a cyclohexyl group and a phenyl group. In the case where $R^1$ and $R^2$ are bonded to each other to form a ring, a tetramethylene group, a pentamethylene group or the like is exemplified. Each of $R^1$ to $R^3$ is preferably a methyl group, an ethyl group, a propyl group or an isopropyl group, and more preferably a methyl group.

$R^4$ and $R^5$ in formula (1) or formula (2) each represents an acyl group having from 10 to 22 carbon atoms or a hydrocarbon group having from 10 to 22 carbon atoms, may be straight-chain or branched, may be saturated or unsaturated, and may be the same or different from each other. The number of carbon atoms in the acyl group or hydrocarbon group is preferably 14 or more, preferably 18 or less, and more preferably 18.

The acyl group having from 10 to 22 carbon atoms constituting each of $R^4$ to $R^5$ includes, for example, a decanoyl group, an undecanoyl group, a dodecanoyl group, a tridecanoyl group, a tetradecanoyl group, a pentadecanoyl group, a hexadecanoyl group, a heptadecanoyl group, an octadecanoyl group, a nonadecanoyl group, an icosanoyl group, a henicosanoyl group, a docosanoyl group, a decenoyl group, an undecenoyl group, a dodecenoyl, a tridecenoyl group, a tetradecenoyl group, a pentadecenoyl group, a hexadecenoyl group, a heputadecenoyl group, a octadecenoyl group, a nonadecenoyl group, an icosenoyl group, a henicosenoyl group, a docosenoyl group, a decadienoyl group, an undecadienoyl group, a dodecadienoyl group, a tridecadienoyl group, a tetradecadienoyl group, a pentadecadienoyl group, a hexadecadienoyl group, a heptadecadienoyl group, an octadecadienoyl group, a nonadecadienoyl group, an icosadienoyl group, a henicosadienoyl group, a docosadienoyl group, an octadecatrienoyl group, an icosatrienoyl group, an icosatetraenoyl group, an icosapentaenoyl group, a docosahexaenoyl group, an isostearyl group and a tetramethylhexadecenyl group (phytol residue), and is preferably a tetradecanoyl group, a tetradecenoyl group, a hexadecanoyl group, a hexadecenoyl group, an octadecanoyl group, an octadecenoyl group or an octadecadienoyl group, and more preferably an octadecanoyl group, an octadecenoyl group or an octadecadienoyl group.

The hydrocarbon group having from 10 to 22 carbon atoms constituting each of $R^4$ to $R^5$ includes, for example, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, henicoseyl group, a docosenyl group, a decadienyl group, an undecadienyl group, a dodecadienyl group, a tridecadienyl group, a tetradecadienyl group, a pentadecadienyl group, a hexadecadienyl group, a heptadecadienyl group, an octadecadienyl group, a nonadecadienyl group, an icosadienyl group, a henicosadienyl group, a docosadienyl group, an octadecatrienyl group, an icosatrienyl group, an icosatetraenyl group, an icosapentaenyl group, a docosahexaenyl group, an isostearyl group, and a tetramethylhexadecenyl group (phytol residue), and is preferably a tetradecyl group, a tetradecenyl group, a hexadecyl group, a hexadecenyl group, an octadecyl group, an octadecenyl group or a octadecadienyl group, and more preferably an octadecyl group, an octadecenyl group or an octadecadienyl group.

$X^-$ in formula (2) represents a halide ion other than an iodide ion, a carboxylate ion or an organic sulfonate ion. $X^-$ specifically includes a chloride ion, a bromide ion, a fluoride ion, an acetate ion, a methanesulfonate ion and a p-toluenesulfonate ion, and is preferably a chloride ion or a methanesulfonate ion, and more preferably a chloride ion.

The cationic lipid represented by formula (2) is obtained by mixing the cationic lipid represented by formula (1) with a tetraalkylammonium salt having X⁻ in an organic solvent to perform anion exchange. The anion exchange is an equilibrium reaction, and by being deposited scarcely soluble tetraalkylammonium iodide by-produced by the anion exchange, the equilibrium of the system is inclined to the side of producing the cationic lipid represented by formula (2). X⁻ of the tetraalkylammonium salt having X⁻ is same as X⁻ of the cationic lipid represented by (2).

As to the tetraalkylammonium salt having X⁻ used in the anion exchange step of the production method of the invention, when the number of carbon atoms of the alkyl group bonded is too large, the tetraalkylammonium iodide by-produced is easily soluble in the organic solvent used in the reaction and the equilibrium is hardly inclined so that the production amount of the cationic lipid represented by formula (2) is decreased. Therefore, the number of the carbon atoms of the alkyl group of the tetraalkylammonium salt is from 1 to 4, preferably from 1 to 2, and more preferably 1.

The tetraalkylammonium salt having X⁻ includes, for example, tetramethylammonium chloride, tetramethylammonium bromide, tetramethylammonium fluoride, tetramethylammonium acetate, tetramethylammonium methanesulfonate, tetramethylammonium p-toluenesulfonate, tetraethylammonium chloride, tetraethylammonium bromide, tetraethylammonium fluoride, tetraethylammonium acetate, tetraethylammonium methanesulfonate, tetraethylammonium p-toluenesulfonate, tetrapropylammonium chloride, tetrapropylammonium bromide, tetrapropylammonium fluoride, tetrapropylammonium acetate, tetrapropylammonium methanesulfonate, tetrapropylammonium p-toluenesulfonate, tetrabutylammonium chloride, tetrabutylammonium bromide, tetrabutylammonium fluoride, tetrabutylammonium acetate, tetrabutylammonium methanesulfonate and tetrabutylammonium p-toluenesulfonate, and is preferably tetramethylammonium chloride, tetramethylammonium bromide, tetramethylammonium fluoride, tetramethylammonium acetate, tetramethylammonium methanesulfonate, tetramethylammonium p-toluenesulfonate, tetraethylammonium chloride, tetraethylammonium bromide, tetraethylammonium fluoride, tetraethylammonium acetate, tetraethylammonium methanesulfonate or a tetraethylammonium p-toluenesulfonate, and more preferably tetramethylammonium chloride, tetramethylammonium bromide, tetramethylammonium fluoride, tetramethylammonium methanesulfonate or tetramethylammonium p-toluenesulfonate.

As to the use amount of the tetraalkylammonium salt having X⁻, when it is too small, the yield of the cationic lipid represented by formula (2) is decreased. When it is too large, the amount of solvent for dissolving the tetraalkylammonium salt having X⁻ is increased so that it is not preferred because the productivity decreases. Therefore, the use amount of the tetraalkylammonium salt having X⁻ is preferably from 1.5 to 10.0 equivalents, more preferably from 2.0 to 5.0 equivalents, to the cationic lipid represented by formula (1).

The organic solvent used in the anion exchange step of the production method of the invention is preferably a protic polar solvent for the purpose of increasing dissociation degree of the cationic lipid represented by formula (1) and ion of the tetraalkylammonium salt. Specifically, a lower alcohol, for example, methanol, ethanol, n-propanol, isopropanol, n-butanol, sec-butanol, isobutanol or tert-butanol is preferred, and ethanol is more preferred.

As to the use amount of the organic solvent used in the anion exchange step of the production method of the invention, when it is too small, stirring is difficult and when it is too large, it is not preferred because the productivity decreases. Specifically, the use amount of the organic solvent is preferably from 5 to 30 times by weight, more preferably from 10 to 20 times by weight, to the cationic lipid represented by formula (1).

The reaction temperature in the production method of the invention is not particularly limited as long as it is a temperature at which the cationic lipid represented by formula (1) and the tetraalkylammonium salt having X⁻ can be dissolved in an organic solvent, and it is ordinarily from 0 to 120° C., and preferably from 10 to 60° C.

According to the production method of the invention, after allowing to react the cationic lipid represented by formula (1) with the tetraalkylammonium salt having X⁻ in an organic solvent, the tetraalkylammonium iodide deposited was separated by filtration, and the filtrate was concentrated by an evaporator to deposit the tetraalkylammonium iodide dissolved in the filtrate, thereby inclining the equilibrium to the system of producing the cationic lipid represented by formula (2) so that the remaining amount of the cationic lipid represented by formula (1) can be further reduced. When the concentration of the filtrate is insufficient and a large amount of the solvent is remained in the concentrate, the cationic lipid represented by formula (1) is remained and the purity of the cationic lipid represented by formula (2) is decreased. Therefore, the weight of the concentrate is preferably 2 times by weight or less, more preferably 1.6 times by weight or less, the charged amount of the cationic lipid represented by formula (1).

The concentrate of the filtrate contains the tetraalkylammonium salt having X⁻ used in excess in addition to the cationic lipid represented by formula (2). In order to remove the tetraalkylammonium salt having X⁻, the concentrate is dispersed in an aprotic solvent which is hard to dissolve the tetraalkylammonium salt having X⁻, and the insoluble matter is separated by filtration. The insoluble matter separated by filtration contains the tetraalkylammonium salt having X⁻ and tetraalkylammonium iodide. Then, the filtrate is subjected to desolventizing to be able to obtain easily the cationic lipid represented by formula (2) of high purity. The aprotic solvent which can be used includes, for example, acetone, acetonitrile, methyl tert-butyl ether, ethyl acetate, chloroform and hexane, and is preferably acetone or ethyl acetate.

As to the use amount of the aprotic solvent, when it is too small, stirring is difficult and when it is too large, it is not preferred because the productivity decreases. Specifically, the use amount of the aprotic solvent is preferably from 5 to 30 times by weight, more preferably from 10 to 20 times by weight, to the cationic lipid represented by formula (1).

The cationic lipid represented by formula (1) is obtained by quaternization of a compound represented by formula (3) with an alkyl iodide.

Formula (3)

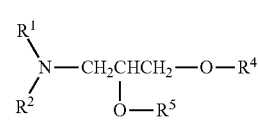

In formula (3), R¹, R², R⁴ and R⁵ each has the same meaning as defined in formula (1) or formula (2).

As to the use amount of the alkyl iodide, when it is too small, the reaction is not completed, and when it is too large, it is not preferred because the productivity decreases. Therefore, the use amount of the alkyl iodide is preferably from 1.1 to 3.0 equivalents, more preferably from 1.2 to 2.0 equivalents, to the compound represented by formula (3).

In the quaternization, a solvent can be used. The solvent used is not particularly limited as long as it dissolves the compound represented by formula (3) and the alkyl iodide and does not inhibit the reaction.

As to the use amount of the solvent in the quaternization, when it is too small, stirring is difficult and when it is too large, it is not preferred because the productivity decreases. Therefore, the use amount of the solvent is preferably from 5 to 30 times by weight, more preferably from 8 to 20 times by weight, to the compound represented by formula (3).

As to the reaction temperature of the quaternization, when it is too low, the reaction does not proceed, and when it is too high, it is not preferred because the side reaction occurs and the yield of the desired product is decreased. Therefore, the reaction temperature of the quaternization is preferably from 0 to 100° C., and more preferably from 20 to 70° C.

The compound represented by formula (3) is obtained by esterification of 3-(dialkylamino)-1,2-propanediol and a fatty acid or etherification of 3-(dialkylamino)-1,2-propanediol and a hydrocarbon having a leaving group. The 3-(dialkylamino)-1,2-propanediol may be appropriately synthesized or a commercially available compound may be used. The commercially available 3-(dialkylamino)-1,2-propanediol includes, for example, 3-(dimethylamino)-1,2-propanediol, 3-(diethylamino)-1,2-propanediol, 3-(dipropylamino)-1,2-propanediol, 3-pyrrolidino-1,2-propanediol, 3-piperidino-1,2-propanediol and 3-(diphenylamino)-1,2-propanediol, and is preferably 3-(dimethylamino)-1,2-propanediol, 3-(diethylamino)-1,2-propanediol or 3-(dipropylamino)-1,2-propanediol, and more preferably a 3-(dimethylamino)-1,2-propanediol.

As to the amount of the fatty acid used in the esterification, when it is too large, the fatty acid remains to reduce the purity of the desired product. When it is too small, the reaction is stopped in the stage of a monoester body to reduce the purity of the desired product. Therefore, the use amount of the fatty acid is preferably from 1.9 to 2.5 equivalents, more preferably from 2.0 to 2.4 equivalents, to the 3-(dialkylamino)-1,2-propanediol.

In the esterification, a condensing agent may be used. As the condensing agent, a carbodiimide condensing agent, an uronium condensing agent, a phosphonium condensing agent or the like can be used, and the carbodiimide condensing agent is preferred from the standpoint of high reactivity and high availability. The carbodiimide condensing agent includes, for example, N, N'-dicyclohexylcarbodiimide, N, N'-diisopropylcarbodiimide and 1-ethyl-3-(3-dimethylaminopropyl)carbodiimide hydrochloride, and 1-ethyl-3-(3-dimethylaminopropyl)carbodiimide hydrochloride is preferred from the standpoint of simplicity of removal after the reaction.

As to the amount of the condensing agent used in the esterification, when it is too large, the formation of an acid anhydride, which is an intermediate, is inhibited. When it is too small, the raw materials remain to decrease the yield. Therefore, the use amount of the condensing agent is preferably from 2.0 to 3.0 equivalents, more preferably from 2.2 to 2.6 equivalents, to the 3-(dialkylamino)-1,2-propanediol.

As the solvent used in the esterification, a solvent which has high solubility of the raw materials from the standpoint of increasing the reaction efficiency and suppressing the formation of by-product. Further, in the case of using 1-ethyl-3-(3-dimethylaminopropyl) carbodiimide hydrochloride as the condensing agent, since urea, which is one of the by-products, can be removed by washing with water, a solvent incompatible with water is preferred. Specifically, chloroform or dichloromethane is preferred.

As to the amount of the solvent used in the esterification, when it is too large, the productivity decreases. When it is too small, the viscosity of the reaction solution increases to cause difficulty in stirring. Therefore, the amount of the solvent is preferably from 30 to 120 times by weight, more preferably from 50 to 100 times by weight, to the 3-(dialkylamino)-1,2-propanediol.

As to the reaction temperature of the esterification, when it is too low, the reaction does not proceed, and when it is too high, an N-acylurea is by-produced to decrease the yield. Specifically, the reaction temperature of the esterification is preferably from 0 to 40° C., and more preferably from 10 to 30° C.

As to the use amount of the hydrocarbon having a leaving group used in the etherification, when it is too large, the hydrocarbon having a leaving group remains to reduce the purity of the desired product. When it is too small, the reaction is stopped in the stage of a monoether body to reduce the purity of the desired product. Therefore, the use amount of the hydrocarbon having a leaving group is preferably from 1.9 to 3.0 equivalents, more preferably from 2.0 to 2.5 equivalents, to the 3-(dialkylamino)-1,2-propanediol.

In the etherification, a base is used as a catalyst. As the base, for example, potassium hydroxide, sodium hydroxide, sodium hydride or potassium tert-butoxide can be used. As to the use amount of the catalyst, when it is too small, the reaction does not proceed, and when it is too large, it is not preferred because the productivity decreases. Therefore, the use amount of the base is preferably from 2.0 to 15.0 equivalents, more preferably from 5.0 to 10.0 equivalents, to the 3-(dialkylamino)-1,2-propanediol.

As the solvent used in the etherification, a solvent which is stable to the base and is incompatible with water is preferred. Specifically, hexane or toluene is preferred, and hexane is more preferred.

As to the reaction temperature of the etherification, when it is too low, the reaction does not proceed, and when it is too high, it is not preferred because the side reaction proceeds and the yield of the desired product is decreased. Specifically, the reaction temperature is preferably from 40 to 120° C., and more preferably from 60 to 100° C.

EXAMPLE (Analysis Method of Iodide Ion Content and Chloride Ion Content)

The iodide ion content and chloride ion content in the cationic lipid represented by formula (2) obtained by the production method of the invention can be confirmed by a potentiometric titration method using, for example, a silver/silver chloride electrode as an electrode and silver nitrate as a titrant. Specifically, about one g of the cationic lipid represented by formula (2) is dissolved in 100 ml of ethanol. In the solution is immersed a silver/silver chloride electrode, and titration is performed by adding an aqueous silver nitrate solution (N/100, N/10) while stirring with a stirrer to measure the potential difference. The potential difference is plotted to the titer, and the iodide ion content can be determined from the titer at the inflection point first appeared (inflection point 1) and the chloride ion content can be determined from the difference between the titer at the second inflection point (inflection point 2) and the titer at the inflection point 1.

Production Example 1

Production of
N-[1-(2,3-dioleoyloxy)propyl]-N,N-dimethylamine
(Hereinafter DODAP)

In 120 g of chloroform were dissolved 2.00 g (16.78 mmol) of 3-(dimethylamino)-1,2-propanediol (product of Tokyo Chemical Industry Co., Ltd), 9.48 g (33.56 mmol) of oleic acid, (EXTRA OLEIN99, product of NOF Corp.) and 0.41 g (3.36 mmol) of 4-dimethylaminopyridine (product of Koei Chemical Co., Ltd.). To the solution was added 7.72 g (40.27 mmol) of 1-ethyl-3-(3-dimethylaminopropyl)carbodiimide hydrochloride (product of Tokyo Chemical Industry Co., Ltd.), followed by stirring at 20 to 30° C. After one hour, the mixture was washed with 120 g of ion-exchanged water and 120 g of an aqueous 25% by weight sodium chloride solution, to the organic layer was added 3.0 g anhydrous magnesium sulfate, followed by stirring. The magnesium sulfate was separated by filtration, and the filtrate was subjected to desolventizing by an evaporator, thereby obtaining DODAP (yield: 11.12 g, 17.16 mmol).

Production Example 2

Production of N-[1-(2,3-dioleoyloxy)propyl]-N,N,
N-trimethylammonium Iodide (Hereinafter DOTAP-I)

In 30 g of acetone was dissolved 3.00 g (4.63 mmol) of DODAP, and to the solution was added 0.99 g (6.94 mmol) of methyl iodide (product of Kanto Chemical Co., Inc.), followed by stirring at 20 to 30° C. After 5 hours, the crystals deposited were separate by filtration and dried, thereby obtaining DOTAP-I (yield: 2.94 g, 3.72 mmol).

Production Example 3

Production of Oleylmethanesulfonate (Hereinafter Ole-Ms)

In 1,450 g of dehydrated toluene was dissolved 290 g (1.08 mol) of oleyl alcohol (NOFABLE (registered trademark) AO-99, product of NOF Corp.), and the solution was cooled to 5 to 10° C. To the solution was added 131 g (1.30 mol) of triethylamine (product of Kanto Chemical Co., Inc.), followed by stirring at 5 to 10° C. for 10 minutes, and then 136 g (1.19 mol) of methanesulfonyl chloride (product of Kanto Chemical Co., Inc.) was slowly added dropwise. After stirring at 5 to 15° C. for one hour, triethylamine hydrochloride deposited was separated by filtration, and the filtrate was washed twice with 580 g of ion-exchanged water. To the organic layer was added 87 g of anhydrous magnesium sulfate, followed by stirring, and then filtering. The filtrate was subjected to desolventizing by an evaporator, thereby obtaining Ole-Ms (yield: 335 g, 0.97 mol).

Production Example 4

Production of
N-[1-(2,3-dioleyloxy)propyl]-N,N-dimethylamine
(Hereinafter DODMA)

To 1168 g of hexane was added 233 g (4.15 mol) of potassium hydroxide (product of Kanto Chemical Co., Inc.), and 55 g (0.46 mol) of 1,2-propanediol (product of Tokyo Chemical Industry Co., Ltd) was added thereto with stirring. Then, 320 g (0.92 mol) of Ole-Ms was added thereto, followed by stirring at 38 to 42° C. After 7 hours, the reaction solution was cooled to 15° C., and washed 3 times with 640 g of distilled water and 256 g of acetonitrile. After further extracting and washing 4 times with 768 g of acetonitrile, the upper layer was subjected to desolventizing by an evaporator, thereby obtaining yellow liquid. The yellow liquid was purified by column chromatography (hexane/ethyl acetate=95/5 to 70/30 (v/v)) using silica gel, thereby obtaining DODMA (yield: 157 g, 0.25 mol).

Production Example 5

Production of N-[1-(2,3-dioleyloxy)propyl]-N,N,N-
trimethylammonium Iodide (Hereinafter DOTMA-I)

In 30 g of acetone was dissolved 3.00 g (4.84 mmol) of DODMA, and to the solution was added 1.03 g (7.26 mmol) of methyl iodide, followed by stirring at 20 to 30° C. After 3 hours, the reaction solution was subjected to desolventizing by an evaporator, thereby obtaining DOTMA-I (yield: 3.70 g, 4.86 mmol).

Example 1

Production of N-[1-(2,3-dioleoyloxy)propyl]-N,N,
N-trimethylammonium Chloride (DOTAP-Cl)

To 20 g of methanol was dissolved 1.39 g (12.66 mmol) of tetramethylammonium chloride (product of Kanto Chemical Co., Inc.), and to the solution was added 2.0 g (2.53 mmol) of DOTAP-I, followed by stirring at 20 to 30° C. After one hour, the crystals deposited were separated by filtration, and the filtrate was concentrated by an evaporator. To the concentrate was added 20 g of ethyl acetate, followed by stirring at 20 to 30° C. After one hour, the insoluble matter was separated by filtration, and the filtrate was subjected to desolventizing, thereby obtaining DOTAP-Cl (yield: 1.65 g, 2.36 mmol).

Example 2

Production of N-[1-(2,3-dioleyloxy)propyl]-N,N,N-
trimethylammonium Chloride (DOTMA-Cl)

To 20 g of methanol was dissolved 1.44 g (13.12 mmol) of tetramethylammonium chloride, and to the solution was added 2.0 g (2.63 mmol) of DOTMA-I, followed by stirring at 20 to 30° C. After one hour, the crystals deposited were separated by filtration, and the filtrate was concentrated by an evaporator. To the concentrate was added 20 g of ethyl acetate, followed by stirring at 20 to 30° C. After one hour, the insoluble matter was separated by filtration, and the filtrate was subjected to desolventizing, thereby obtaining DOTMA-Cl (yield: 1.65 g, 2.36 mmol).

Comparative Example 1

To 35 ml of dichloromethane was dissolved 1.50 g (1.90 mmol) of DOTAP-I. To the solution was added 8 ml of a methanol solution of 1 N hydrochloric acid, followed by stirring at 20 to 30° C. Further, 12 ml of an aqueous 25% by weight sodium chloride solution was added thereto, followed by stirring at 20 to 30° C., and then the organic layer was separated and collected. To the remaining aqueous layer was added 4 ml of dichloromethane, followed by stirring, and the organic layer was collected and mixed with the organic layer previously collected. After repeating 4 times the series of operation from the addition of a methanol solution of 1 N hydrochloric acid, the organic layer collected was washed with 18 ml of an aqueous 25% by weight sodium chloride solution, 5.0 g of anhydrous sodium sulfate was added thereto, followed by stirring, and then filtering. The filtrate was subjected to desolventizing, thereby obtaining a crude product of DOTAP-Cl. The crude product was purified by column chromatography (chloroform/methanol=100/0 to 75/25 (v/v)) using silica gel to remove the by-products, for example, fatty acid, thereby obtaining DOTAP-Cl (yield: 1.26 g, 1.80 mmol).

(Analysis of Iodide Ion Content and Chloride Ion Content in DOTAP-Cl or DOTMA-Cl)

About one g of DOTAP-Cl or DOTMA-Cl obtained in Examples and Comparative Example was dissolved in 100 ml of ethanol. In the solution was immersed a silver/silver chloride electrode, and titration was performed by adding an aqueous silver nitrate solution (N/100, N/10) while stirring with a stirrer to measure the potential difference. The potential difference was plotted to the titer, and the iodide ion content was determined from the titer at the inflection point 1 and the chloride ion content was determined from the difference between the titer at the inflection point 2 and the titer at the inflection point 1.

Figure 2:
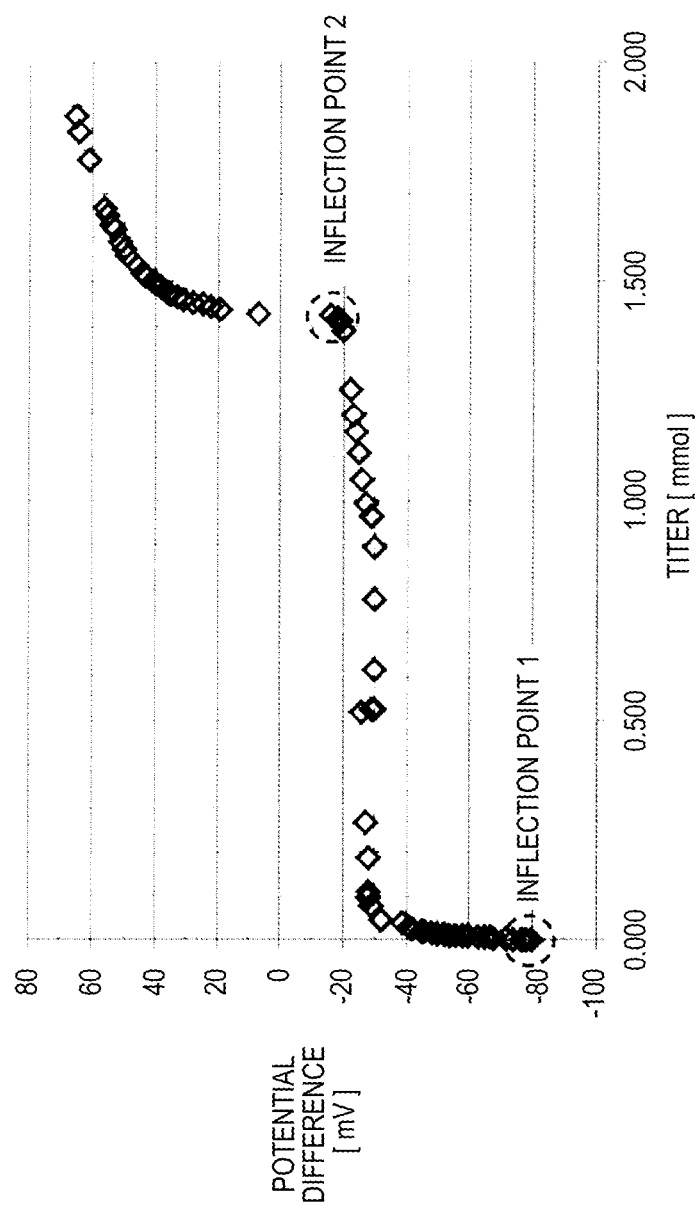
FIG. 2 shows the titration result of DOTMA-Cl obtained in Example 2.
Figure 3:
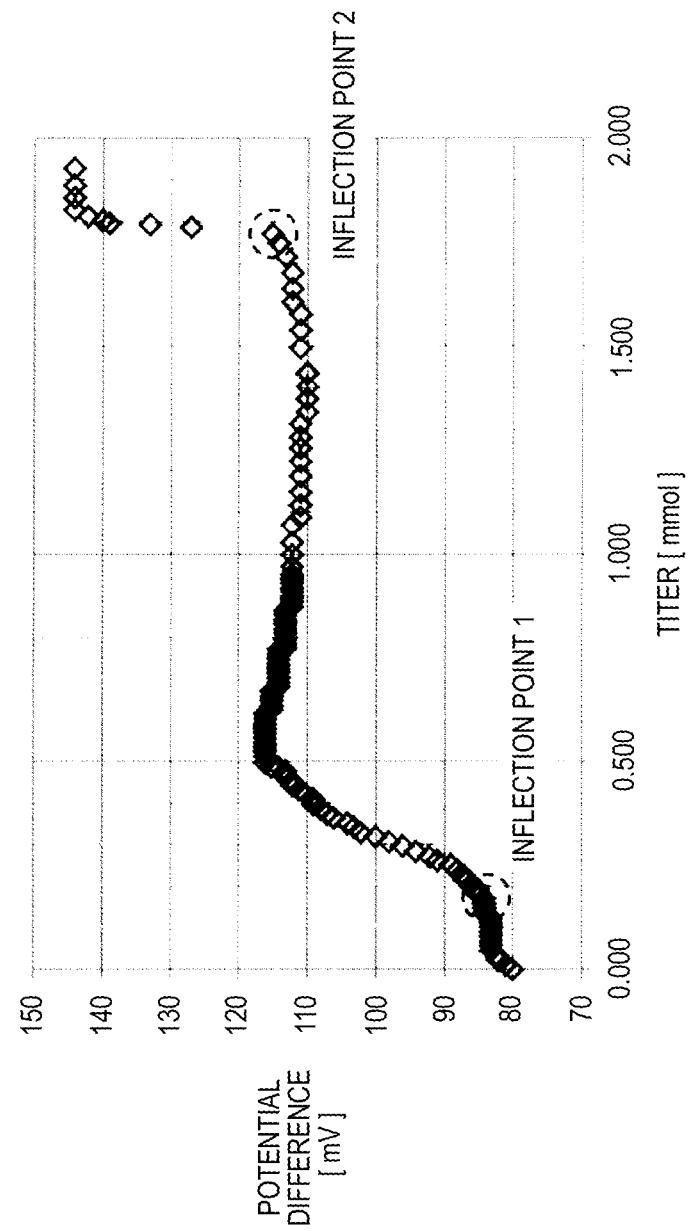
FIG. 3 shows the titration result of DOTAP-Cl obtained in Comparative Example 1.

The analysis results of DOTAP-Cl were plotted (FIGS. 1, 2 and 3). FIG. 1 shows the titration result of DOTAP-Cl obtained in Example 1. FIG. 2 shows the titration result of DOTMA-Cl obtained in Example 2. FIG. 3 shows the titration result of DOTAP-Cl obtained in Comparative Example 1.

With respect to DOTAP-Cl and DOTMA-Cl obtained in Examples 1 and 2 respectively, it can be seen that the iodide ion content is extremely small from the titer (less than 0.001 mmol) at the inflection point 1 immediately after the start of the titration. Further, it can be seen that the chloride ion content contained is almost same as the theoretical value from the difference between the titer at the inflection point 2 and the titer at the inflection point 1, and it is confirmed that the ion exchange proceeds quantitatively and DOTAP-Cl or DOTMA-Cl can be obtained. The chloride ion purity (proportion of the chloride ion to the sum of the iodide ion and the chloride ion) was 99% by mole or more.

On the other hand, with respect to DOTAP-Cl obtained in Comparative Example 1, 0.181 mmol of the iodide ion was contained, and the chloride ion purity was 90% by mole (Table 1). From the results described above, it was confirmed that the production method of the invention is useful as a method for producing a cationic lipid represented by formula (2).

TABLE 1

|  | Amount of Sample (g) | Iodide Ion Content (mmol) | Chloride Ion Content (mmol) | Chloride Ion Purity* (% by mole) |
| --- | --- | --- | --- | --- |
| Example 1 | 1.002 | <0.001 | 1.421 | >99 |
| Example 2 | 0.962 | <0.001 | 1.419 | >99 |
| Comparative Example 1 | 1.264 | 0.181 | 1.567 | 90 |

*Chloride ion content/(Iodide ion content + Chloride ion content) × 100

While the invention has been described in detail and with reference to specific embodiments thereof, it will be apparent to those skilled in the art that various changes and modifications can be made therein without departing from the spirit and scope of the invention.

This application is based on a Japanese patent application filed on Dec. 8, 2014 (Japanese Patent Application No. 2014-247723), and the whole contents thereof are incorporated herein by reference. Also, all the references cited herein are incorporated as a whole.

The invention claimed is:

1. A method for producing a cationic lipid, wherein a cationic lipid represented by formula (1) is mixed with a tetraalkylammonium salt having $X^-$ in an organic solvent, and after separating a tetraalkylammonium iodide deposited by filtration to obtain a filtrate, the filtrate is concentrated to deposit at least a tetraalkylammonium iodide, thereby obtaining a cationic lipid represented by formula (2):

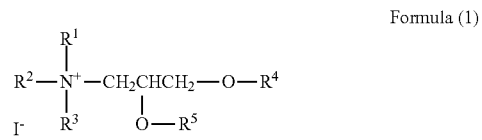

Formula (1)

wherein, in the formula (1), $R^1$, $R^2$ and $R^3$ each represents a hydrocarbon group having from 1 to 6 carbon atoms, and $R^4$ and $R^5$ each represents an acyl having from 10 to 22 carbon atoms or a hydrocarbon group having from 10 to 22 carbon atoms;

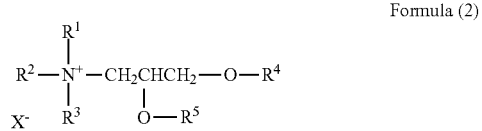

Formula (2)

wherein, in the formula (2), $R^1$, $R^2$ and $R^3$ each represents a hydrocarbon group having from 1 to 6 carbon atoms, $R^4$ and $R^5$ each represents an acyl having from 10 to 22 carbon atoms or a hydrocarbon group having from 10 to 22 carbon atoms, and $X^-$ represents a chloride ion, a bromide ion, a fluoride ion, an acetate ion, a methanesulfonate ion or a p-toluenesulfonate ion.

2. The method as claimed in claim 1, wherein the tetraalkylammonium salt is a tetramethylammonium salt.

3. The method as claimed in claim 1, wherein $X^-$ in the formula (2) is a chloride ion.

4. The method as claimed in claim 2, wherein $X^-$ in the formula (2) is a chloride ion.

* * * * *